(12) United States Patent
Wynn et al.

(10) Patent No.: US 8,007,825 B2
(45) Date of Patent: Aug. 30, 2011

(54) ORAL COMPOSITIONS CONTAINING A SALIVATION INDUCING AGENT

(75) Inventors: David W. Wynn, Huntingdon Valley, PA (US); Ronni Robinson, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 8 days.

(21) Appl. No.: 12/411,638

(22) Filed: Mar. 26, 2009

(65) Prior Publication Data

US 2009/0191267 A1 Jul. 30, 2009

Related U.S. Application Data

(63) Continuation of application No. 11/239,974, filed on Sep. 30, 2005, now abandoned.

(51) Int. Cl.
*A61K 31/4164* (2006.01)
*A61K 31/34* (2006.01)
*A61K 9/28* (2006.01)
*A61K 9/30* (2006.01)

(52) U.S. Cl. ........ 424/464; 424/465; 424/474; 514/397; 514/461; 514/974; 514/960

(58) Field of Classification Search .................. 514/974; 424/464
See application file for complete search history.

(56) References Cited

U.S. PATENT DOCUMENTS

| | | | |
|---|---|---|---|
| 4,173,626 A | 11/1979 | Dempski et al. |
| 4,479,969 A | 10/1984 | Bakai et al. |
| 4,820,506 A | 4/1989 | Kleinberg et al. |
| 4,820,524 A | 4/1989 | Berta |
| 4,851,226 A | 7/1989 | Julian et al. |
| 4,863,742 A | 9/1989 | Panoz et al. |
| 4,906,478 A | 3/1990 | Valentine et al. |
| 4,927,816 A | 5/1990 | Ester |
| 4,980,170 A | 12/1990 | Schneider et al. |
| 4,984,240 A | 1/1991 | Keren-Zvi et al. |
| 5,075,114 A | 12/1991 | Roche |
| 5,156,845 A | 10/1992 | Grodberg |
| 5,228,916 A | 7/1993 | Berta |
| 5,260,072 A | 11/1993 | Roche et al. |
| 5,275,822 A | 1/1994 | Valentine et al. |
| 5,286,497 A | 2/1994 | Hendrickson et al. |
| 5,387,614 A | 2/1995 | Schoenwald et al. |
| 5,489,436 A | 2/1996 | Hoy et al. |
| 5,571,528 A | 11/1996 | Lee et al. |
| 5,580,880 A | 12/1996 | Handa et al. |
| 5,912,013 A | 6/1999 | Rudnic et al. |
| 5,948,430 A | 9/1999 | Zerbe et al. |
| 5,962,503 A | 10/1999 | Ekstrom et al. |
| 6,090,401 A | 7/2000 | Gowan, Jr. et al. |
| 6,103,260 A | 8/2000 | Luber et al. |
| 6,177,096 B1 | 1/2001 | Zerbe et al. |
| 6,258,381 B1 | 7/2001 | Luber et al. |
| 6,270,790 B1 | 8/2001 | Robinson et al. |
| 6,270,805 B1 | 8/2001 | Chen et al. |
| 6,277,409 B1 | 8/2001 | Luber et al. |
| 6,322,819 B1 | 11/2001 | Burnside et al. |
| 6,419,903 B1 | 7/2002 | Xu et al. |
| 6,432,442 B1 | 8/2002 | Buehler et al. |
| 6,596,298 B2 | 7/2003 | Leung et al. |
| 6,709,678 B2 | 3/2004 | Gruber |
| 6,837,696 B2 | 1/2005 | Sowden et al. |
| 2002/0068088 A1 | 6/2002 | Gruber |
| 2002/0122778 A1 | 9/2002 | Wolfson |
| 2003/0070584 A1 | 4/2003 | Gulian et al. |
| 2003/0072729 A1 | 4/2003 | Szymczak et al. |
| 2003/0072731 A1 | 4/2003 | Guilian et al. |
| 2004/0247675 A1 | 12/2004 | Gruber |
| 2006/0029665 A1 | 2/2006 | Singh |

FOREIGN PATENT DOCUMENTS

| | | |
|---|---|---|
| EP | 1219291 | 3/2002 |
| FR | 2 864 01 A | 7/2005 |
| WO | WO 88/06893 A1 | 9/1988 |
| WO | WO 00/25744 | 5/2000 |
| WO | WO 01/54499 A1 | 8/2001 |
| WO | WO 02/49607 A | 6/2002 |
| WO | WO 02/80886 A1 | 10/2002 |
| WO | WO 2004/096174 A | 11/2004 |
| WO | WO 2005/063203 A | 7/2005 |

OTHER PUBLICATIONS

Yashiro et al., "Changes in microsomal lysophospholipid acyltransferase activity are correlated with rat parotid gland enlargement induced by chronic administration of isoproterenol," J. Biochem., 115, 1040-1046 (1994).
Webber, M et. al., "Atropine as a possible agent to prevent Xerostomia in patients treated with iodine-131 for carcinoma of thyroid," Journal of Nuclear Medicine, vol. 12, No. 6, Jun. 1971, pp. 482-483.
Bagheri et al., "Pharmacokinetic Study of yohimbine and its pharmacodynamic effects on salivary secretion in patients treated with tricyclic antidepressants," British Jl. Clinical Pharmacology, 1994; 37, pp. 93-96.
Bruck et al., "Xerostomie and asialia caused by psychotropic drugs and treatment with TPMP," NR.33-35 Wien Med Wochenschr 495-500 (Aug. 17, 1974). ("Bruck").
Levin, S. L., "Salivation from the denervated Human Parotid gland induced by Pirenzepine and Telenzepine," Eur. Jl. Clinical Pharmacology, (1991)41, pp. 613-614.
Kawashiro et. al., "Pharmacokinetics of SNI-2011 (2): Absorption, Restriction, Excretion and Metabolism of 14C-SNI-2011 in Dogs," Xenobio. Metabol. and Dispos., 16(6): 553-557 (2001).
USP 24, 2000 Version, pp. 19-20 and p. 856 (1999).
Lachman, et al., The Theory and Practice of Industrial Pharmacy, Chapter 11 ($3^{rd}$ Ed. 1986).

(Continued)

*Primary Examiner* — James Anderson
*Assistant Examiner* — Gregg Polansky

(57) ABSTRACT

Oral dosage forms, and particles used therein, containing salivation inducing agents are disclosed. The salivation agents may be in the core of the dosage form and/or in coatings applied thereto, or alternatively may be within particles and/or the matrix of such dosage forms, in coatings applied to such particles, or on the surface of such coated particles. The particles may be produced into a tablet form, such as a chewable tablet form, that provides for the immediate release of the active ingredient. Other oral dosage forms include thin film strips, gummi, foam tabs, and lozenges.

18 Claims, No Drawings

OTHER PUBLICATIONS

Lieberman, et. Al., "Pharmaceutical Dosage Forms—Tablets," vol. 2, pp. 213-217 and 327-329 (2nd ed 1990).

Bruck (English Translation).

Fox, "Salivary Enhancement Therapies", *Caries Research*, vol. 38, No. 3 (May 2004) pp. 241-246.

Iwabuchi et al, "Sialogogic Activities of SNI-2011 Compared with those of Pilocarpine and McN-A-343 in Rat Salivary Glands: Identification of a Potential Therapeutic Agent for Treatment of Sjorgen's Syndrome", *General Pharmacology*, vol. 25, No. 1 (Jan. 1994) pp. 123-129.

US 8,007,825 B2

ORAL COMPOSITIONS CONTAINING A SALIVATION INDUCING AGENT

This is a continuation of prior U.S. application Ser. No. 11/239,974, filed Sep. 30, 2005 now abandoned, which is incorporated by reference herein in its entirety.

FIELD OF THE INVENTION

This invention relates to oral compositions containing an active ingredient and a salivation inducing agent. These compositions may be used to make dosage forms that conveniently may be administered without water.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Chewable tablets are typically made from a mixture including active drug particles, and other inactive ingredients (excipients), and are often employed for the administration of pharmaceuticals where it is impractical to provide a tablet for swallowing whole. With chewable tablets, the act of chewing helps to break up the tablet particles as the tablet disintegrates and may increase the rate of absorption by the digestive tract. Chewable tablets are often utilized to improve drug administration in pediatric and geriatric patients.

Various attempts have been made to enhance the texture of drug particles in order to prevent their adhesion to the oral mucosa upon ingestion. For example, WO88/06893 discloses an oral composition comprised of an active substance and a gelling or swelling agent capable of forming a viscous medium around the particles in an aqueous carrier. Disadvantageously, such compositions must be disintegrated in water to form a liquid suspension before ingestion for purposes of facilitating the ease of quickly swallowing the composition without chewing. U.S. Pat. No. 6,709,678 has overcome the need to suspend the formulation in an aqueous vehicle before administration by coating its particles with a hydratable polymer and a salivation-promoting agent.

It would be desirable to have an oral dosage form that effectively increases saliva production during ingestion, which thereby obviates the need for consumption with water and thereby improves the swallowability of such dosage forms.

SUMMARY OF THE INVENTION

The present invention provides for pharmaceutical compositions as disclosed in the claims.

In accordance with this invention, various forms of pharmaceutical formulations having an immediate release profile may be made using a salivation inducing agent. The initiation of an increased amount of saliva not only facilitates the swallowing of the dosage form, but it also provides for convenient ingestion without the need for water.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Unless defined otherwise, all ranges provided herein also explicitly include all range combinations that may be formed by all numbers within the endpoints of the range.

As used herein, "injection molding" shall mean a process of forming a dosage form in a desired shape and size wherein a flowable material, which is in a fluid or flowable state form, enters a mold, then is solidified in the mold via a change in temperature (either positive or negative) before being removed therefrom. By contrast, "compression," as used herein, shall mean a process of forming a dosage form in a desired shape and size wherein a material is compacted into a tablet between the surfaces of punches via an increase in pressure before being removed therefrom.

As used herein, an "exterior surface" of a portion is a surface that comprises part of the exterior surface of the finished dosage form.

As used herein, the term "substantially covers" or "substantially continuous" means that the coating is generally continuous and generally covers the entire surface of the core or underlying layer, so that little to none of the active ingredient or underlying layer is exposed.

As used herein, the term "salivation inducing agent" shall mean a tasteless compound that has a salivation-inducing value of at least about 10%, e.g. at least about 12% or at least about 16% or at least about 18%, and which substantially excludes the following water soluble components: a) water-soluble acids such as tartaric acid, citric acid, malic acid, fumaric acid, and ascorbic acid; b) water-soluble salts such as sodium or potassium chloride, sodium or potassium hydrogen tartarate, sodium hydrogen citrate or sodium ascorbate; and c) water-soluble substances having an osmotic action such as glucose, fructose, sucrose, xylitol, mannitol; sorbitol, maltitol and mixtures thereof. By "substantially excludes," it means that the resulting formulation contains less than about 0.1 percent, e.g. less than about 0.5 percent or less than about 0.01 percent or less than 0.001 percent of such water soluble components.

Examples of suitable salivation inducing agents include, but are not limited to, those tasteless muscarinic acetylcholine receptor agonists such as pilocarpine and the compound that is commercially available from IFF under the tradename, "SN12011;" sigma sigma binders such as arylalkylamines wherein the alkyl group has from about 1 to about 8 carbons, i.e., e.g., N,N-disubstituted phenylalkylamines wherein the alkyl has from about 1 to about 8 carbons and N,N disubstituted-2-phenylcyclopropylamines; spirooxathiolane-quinnuclidine; Heliopsis longpipes root; cholinesterase inhibitors; and mixtures thereof.

As used herein, "tasteless" shall mean the substantial absent of or not substantially contributing to a sense of flavor, sweetness, saltiness, bitterness or sourness.

As used herein, "salivation inducing value" is the amount of additional saliva, expressed in percentage terms, secreted in the mouth of a user who consumes a dosage form containing a compound that may be a salivation inducing agent in accordance with the test method set forth in Example 3, relative to the amount of saliva secreted in the mouth of a user who similarly consumes a tablet containing the same ingredients but without that compound, after a period of about 30 seconds, e.g. after about 1 minute or about 3 minutes or about 5 minutes, after either swallowing the tablet or removing the tablet from the user's mouth.

As used herein, "sweetness index" is a term used to describe the level of sweetness of the dosage form relative to sucrose. Sucrose, defined as the standard, has a sweetness index of 1. For example, the sweetness indices of several known sweetener compounds are listed below:

| | |
|---|---|
| Sorbitol | 0.54-0.7 |
| Dextrose | 0.6 |
| Mannitol | 0.7 |
| Sucrose | 1.0 |
| High Fructose Corn Syrup 55% | 1.0 |
| Xylitol | 1.0 |
| Fructose | 1.2-1.7 |
| Cyclamate | 30 |
| Aspartame | 180 |
| Acesulfame K | 200 |
| Saccharin | 300 |
| Sucralose | 600 |
| Talin | 2000-3000 |

In one embodiment, the dosage form of the present invention may be provided with a sweetness index less than about 0.6. The addition of sweetening agent may increase the sweetness of the dosage form to at least about 0.9, e.g. at least about 1.0, say at least about 1.5, or at least about 2.0.

As used herein, the term "dosage form" applies to any ingestible forms that are designed to be chewed or remain in the mouth of a user, as opposed to those forms that are designed to be immediately swallowed upon ingestion. Examples of suitable ingestible forms include, but are not limited to solid, dosage forms having a liquid, powder or solid core; chewable or oral disintegrating tablets; thin strips; gummi tablets; foam tablet; and coated particles having the salivation inducing agent in the coating and/or granulation matrix. In one embodiment, dosage forms are solid, semisolid, or liquid compositions designed to contain a specific pre-determined amount (i.e. dose) of a certain ingredient, for example an active ingredient as defined below. Suitable dosage forms may be pharmaceutical drug delivery systems, including those for oral administration, buccal administration, or mucosal delivery; or compositions for delivering minerals, vitamins and other nutraceuticals, oral care agents, flavorants, and the like. In one embodiment, the dosage forms of the present invention may be considered to be solid; however, they may contain liquid or semi-solid components. In another embodiment, the dosage form is an orally administered system for delivering a pharmaceutical active ingredient to the gastro-intestinal tract of a human. In yet another embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient. "Active ingredients," as used herein, includes, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof. Suitable oral care agents include breath fresheners, tooth whiteners, antimicrobial agents, tooth mineralizers, tooth decay inhibitors, topical anesthetics, mucoprotectants, and the like. Suitable flavorants include menthol, peppermint, mint flavors, fruit flavors, chocolate, vanilla, bubblegum flavors, coffee flavors, liqueur flavors and combinations and the like. Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for H. pylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine. In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof. In another embodiment, the active ingredient may be selected from analgesics, anti-inflammatories, and antipyretics: e.g. nonsteroidal anti-inflammatory drugs (NSAIDs), including propionic acid derivatives: e.g. ibuprofen, naproxen, ketoprofen and the like; acetic acid derivatives: e.g. indomethacin, diclofenac, sulindac, tolmetin, and the like; fenamic acid derivatives: e.g. mefanamic acid, meclofenamic acid, flufenamic acid, and the like; biphenylcarbodylic acid derivatives: e.g. diflunisal, flufenisal, and the like; and oxicams: e.g. piroxicam, sudoxicam, isoxicam, meloxicam, and the like. In one embodiment, the active ingredient is selected from propionic acid derivative NSAID: e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from pseudoephedrine, phenylepherine, phenylpropanolamine, chlorpheniramine, dextromethorphan, diphenhydramine, guaifenesin, astemizole, terfenadine, fexofenadine, loratadine, desloratidine, doxilamine, norastemizole, cetirizine, benzocaine, mixtures thereof and pharmaceutically acceptable salts, esters, isomers, and mixtures thereof.

In another embodiment, the active ingredient may be methylphenidate, modafinil and other active agents suitable for attention deficit hyperactivity disorder or attention deficit disorder; oxybutynin; sidenefil; and cyclobenzaprine.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient or ingredients are present in the dosage forms of the present invention in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. In one embodiment, the dosage form comprises at least about 85 weight percent of the active ingredient. The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1 micron to about 2000 microns. In one embodiment, such particles are crystals having an average particle size of about 1 micron to about 300 microns. In yet another embodiment, the particles are granules or pellets having an average particle size of about 50 microns to about 2000 microns, e.g. from about 50 microns to about 1000 microns or from about 100 microns to about 800 microns.

In certain embodiments in which modified release of the active ingredient is desired, the active ingredient may optionally be coated with a known release-modifying coating. This advantageously provides an additional tool for modifying the release profile of active ingredient from the dosage form. For example, the dosage form may contain coated particles of one or more active ingredients, in which the particle coating confers a release modifying function, as is well known in the art. Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release active ingredients may also be employed. For example, acetaminophen particles, which are encapsulated with release-modifying polymers by a coaccervation process, may be used in the present invention. Such coaccervation-encapsulated acetaminophen is commercially available from, for example, Eurand America, Inc. or Circa Inc.

If the active ingredient has an objectionable taste, and the dosage form is intended to be chewed or disintegrated in the mouth prior to swallowing, the active ingredient may be coated with a taste masking coating, as known in the art. Examples of suitable taste masking coatings are described in, for example, U.S. Pat. Nos. 4,851,226; 5,075,114; and 5,489,436. Suitable processes for applying taste-masked coatings to dosage forms are known in the art, and include but are not limited to, fluid bed coating, coaccervation, complex coaccervation, spray drying and spray congealing. Commercially available taste masked active ingredients may also be employed. For example, acetaminophen particles, which are encapsulated with ethylcellulose or other polymers by a coaccervation process, may be used in the present invention. Such coaccervation-encapsulated acetaminophen is commercially available from Eurand America, Inc. or Circa Inc.

The active ingredient or ingredients are typically capable of dissolution upon contact with a fluid such as water, stomach acid, intestinal fluid or the like. In one embodiment, the dissolution characteristics of the active ingredient meet USP specifications for immediate release tablets containing the active ingredient. In embodiments in which it is desired for the active ingredient to be absorbed into the systemic circulation of an animal, the active ingredient or ingredients should be capable of dissolution upon contact with a fluid such as water, gastric fluid, intestinal fluid or the like. In one embodiment, the dissolution characteristics of the active ingredient meet USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the active ingredient may be modified: e.g. controlled, sustained, extended, retarded, prolonged, or delayed.

The location of the salivation agent within the dosage form is not critical, and will depend upon, for example, the type of dosage form selected, active agent selected, processing steps desired, and the like. For example, the salivation agent may be in the core of a dosage form or in one or more coatings applied to the core of the dosage form. In another embodiment, the salivation agent may be in coatings for active ingredient granules and/or in the granulation matrix therefore, which are then compacted or extruded to yield a dosage form.

In addition to the active ingredient and the salivation inducing agent, the dosage form may contain other optional ingredients including, but are not limited to fillers, including water soluble compressible carbohydrates such as sucrose, mannitol, sorbitol, maltitol, xylitol, erythritol, lactose, isomalt, lactitiol, dextrose, polydextrose, dextrose monohydrate, fructose, maltose and mixtures thereof; conventional dry binders including cellulose, cellulosic derivatives, polyvinyl pyrrolidone, starch, modified starch, maltodextrin, and mixtures thereof, and in particular microcrystalline cellulose, maltodextrin, and starch; sweeteners including aspartame, acesulfame potassium, sucralose and saccharin; disintegrants such as microcrystalline cellulose, starch, sodium starch glycolate, crosslinked polyvinylpyrrolidone, crosslinked carboxymethylcellulose; preservatives, flavors, acidulants, antioxidants, glidants, surfactants, and coloring agents.

The dosage forms of the present invention may be made by any means known in the art. For example, conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., "The Theory and Practice of Industrial Pharmacy," Chapter 11, ($3^{rd}$ Ed. 1986), which is incorporated by reference herein. In embodiments wherein the tablets are formed by the direct compression method, the desired blend of active ingredients, salivation inducing agent, and optional ingredients are blended, then a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

One embodiment of the present invention is directed to a dosage form having a core substantially covered with a coating, wherein the coating is comprised of, based upon the total weight of the coating, from about 0.01 percent to about 15 percent, for example, from about 0.1 percent to about 5 percent of a salivation inducing agent. Suitable ingredients for coatings and methods for applying such coatings to tablet cores, such as, for example, via dip coating, spray coating, or injection molding, are known in the art and disclosed in, for example, United States Publication Nos. 20030072729, 0072731, and 0070584; and U.S. Pat. Nos. 4,820,524, 5,228,916; and 6,837,696.

Another embodiment of the present invention is directed to a chewable dosage form having particles of active agents that are optionally covered with a taste masking and/or texture masking coating. Examples of suitable taste masking and/or texture masking agents are known in the art and disclosed in, for example, U.S. Pat. Nos. 4,851,226, 5,260,072 and 5,075,114. In this embodiment, the salivation inducing agent may be present in the matrix in an amount, based upon the total dry weight of the dosage form, from about 0.01 percent to about 10 percent, e.g., from about 0.05 percent to about 5 percent. The salivation inducing agent may also be within the granulated active agent particle, and/or within the coating applied to the particles in an amount, based upon the total dry weight of the coated particle, from about 0.1 percent to about 25 percent, e.g., from about 0.1 percent to about 15 percent. In embodiments wherein the salivation inducing agent is applied to a particle of an active ingredient that has been previously coated with an initial coating taste masking and/or texture masking coating, the dosage form contains, based upon the total dry weight of the particle coated with an initial coating as well as a salivation inducing agent coating, from about 0.1 percent to about 25 percent, e.g., from about 0.1 percent to about 15 percent of a salivation inducing agent. Suitable additional ingredients for chewable dosage forms and methods for their manufacture are well known in the art and disclosed in, for example, U.S. Pat. Nos. 6,277,409, 6,270,790, and 6,258,381. For example, the chewable dosage form may contain an active ingredient, a salivation inducing agent, a sweetener such as sucrose, and any of the above-mentioned compressible carbohydrate including, but not limited to dextrose monohydrate, lactose, mannitol and xylitol.

In embodiments wherein a chewable tablet is desired, the degree of particle compaction is controlled so that the resulting tablets are relatively soft, i.e. they have a hardness of up to about 15 kiloponds per square centimeter (kp/cm$^2$), e.g. from about 1 kp/cm$^2$ to about 10 kp/cm$^2$ or from about 2 kp/cm$^2$ to about 6 kp/cm$^2$. "Hardness" is a term used in the art to describe the diametrical breaking strength as measured by conventional pharmaceutical hardness testing equipment, such as a Schleuniger Hardness Tester. In order to compare values across different size tablets, the breaking strength is normalized for the area of the break (which may be approximated as the tablet diameter times the thickness). This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329 (hereinafter "Lieberman").

In another embodiment, the dosage form may be comprised of a thin film strip containing, based upon the total dry weight of the dosage form, from about 0.1 percent to about 10 percent, e.g., from about 0.1 percent to about 5 percent of a salivation inducing agent. Suitable ingredients for thin film strip dosage forms and methods for their products are well known in the art and disclosed in, for example, U.S. Pat. Nos. 6,177,096; 5,948,430; U.S. Pat. No. 6,596,298 and U.S. Pat. No. 6,419,903. As used herein, "thin film strip" shall mean a dosage form that rapidly disintegrates in the oral cavity subsequent to ingestion and that comprises at least one water soluble polymer and optionally one active ingredient, wherein the thickness of the dosage form is less than 200 microns.

In another embodiment, the dosage form may be comprised of a gummi dosage form containing, based upon the total dry weight of the dosage form, from about 0.1 percent to about 10 percent, e.g., from about 0.1 percent to about 5 percent of a salivation inducing agent. Suitable ingredients for gummi dosage forms and methods for their products are well known in the art and disclosed in, for example, U.S. Pat. No. 6,432,442. As used herein, "gummi" dosage forms shall mean an edible dosage form suitable for human consumption having a gel-like matrix comprised of gelatin, one or more hydrocolloids, and an optional active ingredient, such that the dosage form is chewed and swallowed in less than 20 seconds. Such gummi dosage forms may also optionally contain sweeteners, adjuvants and flavorants such as those aforementioned.

In another embodiment, the dosage form may be comprised of a foam tab dosage form containing, based upon the total weight of the dry dosage form, from about 0.1 percent to about 10 percent, e.g., from about 0.1 percent to about 5 percent of a salivation inducing agent. Suitable ingredients for foam tab dosage forms and methods for their products are well known in the art and disclosed in, for example, U.S. Pat. No. 6,090,401. As used herein, "foam tab" dosage forms shall mean an edible dosage form suitable for human consumption having a density less than 0.40 grams per cubic centimeter comprising a polymeric foaming agent such as, for example, hypromellose, a polysaccharide and optionally an active ingredient. Such foam tab dosage forms may also optionally contain sweeteners, adjuvants and flavorants such as those aforementioned.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Preparation of Chewable Tablet without Salivary Inducing Agent

A blend for chewable tablets was prepared using the materials described in Table 1.

TABLE 1

Chewable Tablet Formulation

| Ingredients | Trade Name | Manufacturer | Mg/Tablet |
|---|---|---|---|
| Sucralose Powder NF | | Tate and Lyle | 10.0 |
| Dextrose Monohydrate NF | | | 957.3 |
| Crospovidone NF | Polyplasdone XL-10 | International Specialty Products | 16.7 |
| Magnesium Stearate NF | | | 8.0 |

TABLE 1-continued

Chewable Tablet Formulation

| Ingredients | Trade Name | Manufacturer | Mg/Tablet |
|---|---|---|---|
| Peppermint Flavor | | International Flavors and Fragrances | 8.0 |
| Total | | | 1000.0 |

The dextrose monohydrate was screened through a 20 mesh screen, then approximately half was added to a plastic bottle. The sucralose powder, peppermint flavor, and crospovidone were screened through a 50 mesh screen, then added to the plastic bottle. One half of the remaining portion of dextrose monohydrate was screened through the 50 mesh screen, then added to the plastic bottle. All remaining, unscreened dextrose monohydrate was then added to the plastic bottle. The components were blended end-over-end in the plastic bottle for 3 minutes.

The magnesium stearate was then screened through a 50 mesh screen and added to the bottle. The bottle was blended end-over-end for an additional minute, then compressed to a hardness of approximately 6.3 kiloponds on a rotary tablet press equipped with ⅝ inch round flat-faced beveled edge tooling.

Example 2

Preparation of Chewable Tablet Containing Salivary Inducing Agent

A blend for chewable tablets containing a salivary inducing agent was prepared using the materials described in Table 2 below:

TABLE 2

Chewable Tablet Formulation

| Ingredients | Trade Name | Manufacturer | Mg/Tablet |
|---|---|---|---|
| Sucralose Powder NF | | Tate & Lyle | 10.0 |
| Dextrose Monohydrate NF | | | 956.3 |
| Crospovidone NF | Polyplasdone XL-10 ® | International Specialty Products | 16.7 |
| Magnesium Stearate NF | | | 8.0 |
| Peppermint Flavor | | International Flavors and Fragrances | 8.0 |
| Salivary Inducing Agent | | International Flavors and Fragrances | 1.0 |
| Total | | | 1000.0 |

The dextrose monohydrate was screened through a 20 mesh screen, then approximately half was added to a plastic bottle. The sucralose powder, peppermint flavor, crospovidone, and salivary inducing agent were then screened through a 50 mesh screen and added to the plastic bottle. One half of the remaining portion of dextrose monohydrate was screened through the 50 mesh screen, then added to the bottle. After all remaining dextrose monohydrate was added to the plastic bottle, the components were blended end-over-end in the plastic bottle for 3 minutes. After the magnesium stearate was screened through a 50 mesh screen, it was added to the bottle, which was blended end-over-end for an additional minute. The blend was then compressed into tablets with a hardness of approximately 6.3 kiloponds on a rotary tablet press equipped with ⅝ inch round flat-faced beveled edge tooling.

Example 3

Method for Determining Salivation Inducing Agent

A panelist received a tablet, which was produced in accordance with Example 1, and was instructed to chew the tablet and to expectorate (instead of swallow) their saliva into a graduated cylinder as they slowly swallowed the tablet. At intervals of 30 seconds, two minutes, three minutes, and five minutes after the tablet was swallowed, the amount of expectorated saliva was measured. The panelist waits four hours, then repeats the procedure with a second tablet, which was produced in accordance with Example 2.

Ten additional, independent panelists repeated this procedure. The results are set forth below in Tables 3 and 4.

TABLE 3

Amount of Expectorated Saliva

| Panelist # | 30 Seconds | | 2 Minutes | | 3 Minutes | | 5 Minutes | |
|---|---|---|---|---|---|---|---|---|
| | $1^{st}$ Tablet (ml) | $2^{nd}$ Tablet (ml) | $1^{st}$ Tablet (ml) | $2^{nd}$ Tablet (ml) | $1^{st}$ Tablet (ml) | $2^{nd}$ Tablet (ml) | $1^{st}$ Tablet (ml) | $2^{nd}$ Tablet (ml) |
| 1 | 0.5 | 0.5 | 1.5 | 1.4 | 2.0 | 2.0 | 3.0 | 3.5 |
| 2 | 1.1 | 1.3 | 2.6 | 3.6 | 3.3 | 4.4 | 4.4 | 7.3 |
| 3 | 0.2 | 1.0 | 1.6 | 2.1 | 2.6 | 2.4 | 3.5 | 2.9 |
| 4 | 0.6 | 0.8 | 1.0 | 1.2 | 0.3 | 1.0 | 1.0 | 1.5 |
| 5 | 1.4 | 1.8 | 1.8 | 3.7 | 3.8 | 4.8 | 5.6 | 8.4 |
| 6 | 0.4 | 0.9 | 1.3 | 2.5 | 2.2 | 3.0 | 4.4 | 4.8 |
| 7 | 0.3 | 0.5 | 0.5 | 0.9 | 0.8 | 1.0 | 0.9 | 1.0 |
| 8 | 0.5 | 0 | 2.0 | 2.3 | 2.5 | 2.7 | 3.5 | 3.5 |
| 9 | 0.8 | 1.0 | 1.8 | 1.9 | 2.1 | 2.8 | 3.0 | 3.5 |
| 10 | 1.5 | 1.0 | 3.5 | 2.5 | 4.7 | 4.2 | 7.2 | 7.0 |
| 11 | 12.0 | <1 | 2.5 | 2.5 | 3.0 | 3.1 | 3.9 | 4.1 |

TABLE 4

Difference in Saliva Production

Difference in saliva production by second tablet relative to amount of saliva produced by first tablet (%)

| Panelist | 30 seconds | 1 minute | 3 minutes | 5 minutes |
|---|---|---|---|---|
| 1 | 0 | −7.1 | 0 | 14.3 |
| 2 | 15 | 27.8 | 25.0 | 39.7 |
| 3 | 80 | 23.8 | −8.3 | −20.7 |
| 4 | 25 | 16.7 | 70.0 | 33.3 |
| 5 | 22 | 51.4 | 20.8 | 33.3 |
| 6 | 56 | 48.0 | 26.7 | 8.3 |
| 7 | 40 | 44.4 | 20.0 | 10.0 |
| 8 | 0 | 13.0 | 7.4 | 0 |
| 9 | 20 | 5.3 | 25.0 | 14.3 |
| 10 | −50 | −40.0 | −11.9 | −2.9 |
| 11 | 0 | 0.0 | 3.2 | 4.9 |
| Average | 18.92 | 16.66 | 16.17 | 12.24 |

This Example showed that 8 out of the 11 panelists had increased saliva generation with the second tablet, which contained a salivation inducing agent, relative to the first tablet which did not.

This Example also showed that the second tablet, which contained the salivation inducing agent, generated an average in excess of 18 percent more saliva than the amount generated by the first tablet, when the saliva generated from each tablet was measured 30 seconds after swallowing each respective tablet.

For dosage forms that are designed to remain in the mouth of a user, such as a lozenge, this test can be modified so that the user removes such dosage form from the mouth 30 seconds after placing it therein. The amount of saliva produced can then be measured for any interval after the dosage form is removed.

Example 4

Production of Thin-Film Dosage Form Containing Salivary Inducing Agent

TABLE 5

Preparation of the Thin-Film Base

| Ingredients | Percent (w/w) | mg/strip |
|---|---|---|
| Acetaminophen | 26.67 | 80.00 |
| Hydroxypropylmethylcellulose (HPMC 5) cps | 62.68 | 188.04 |
| Carrageenan | 1.00 | 3.00 |
| Propylene Glycol | 7.00 | 21.00 |
| Citric Acid USP (anhydrous) | 0.75 | 2.25 |
| Sodium Benzoate NF | 0.30 | 0.90 |
| Flavor NF | 1.00 | 3.00 |
| Sucralose Powder NF | 0.50 | 1.50 |
| Salivary Inducing Agent | 0.10 | 0.30 |
| Deionized (DI) Water* | 0.00 | — |
| TOTAL | 100.0 | 300.0 |

*Deionized Water removed upon drying.

The materials in the table above are processed into a thin film using the following procedure.

For every 10.0 grams of total materials for the thin-film mixture in Table A, 90.0 grams of DI water is required to create a dispersion that contains approximately 10% solids. The water is first heated to 85° C. To prepare the thin-film dosage form, the sodium benzoate, flavor, sucralose, salivary inducing agent and citric acid are added to the DI water until dissolved using a lab scale mixer at 500 RPM. The HPMC and carrageenan are then added while mixing at 500 RPM. The acetaminophen is then added and dispersed while mixing.

The mixture is then poured manually into pre-formed molds designed to produce thin-film dosage forms having a thickness of about 70 microns and a dry weight of approximately 300.0 mg under a constant temperature of 10° C. The thin-film dosage forms are then removed from the molds and dried at 50° C. and 40% relative humidity until the water is substantially removed.

Example 5

Preparation of Coating Solution with Salivation Inducing Agent

A film coating solution is prepared by adding to a beaker containing ethanol and purified water in a 50:50 weight ratio the following solid ingredients in order and under ambient conditions: hydroxypropylmethylcellulose (5 centipoise grade); polyethylene glycol 8000; and talc. The finished solution contains 10.0% of solids, relative to the total weight of the coating solution.

The salivary inducing agent is then added thereto and mixed at 500 RPM for 1 hour under ambient conditions. The solution is allowed to deaerate for a minimum of 2 hours prior to use. The final coating solution contains the ingredients set forth below in Table 6 in amounts based upon the weight percent of the final coating solution:

TABLE 6

Composition of Coating Solution

| Component | Weight Percent |
|---|---|
| Polyethylene Glycol 8000 | [60] . . . 57.6% |
| Hydroxypropylmethylcellulose 5 cps | [40] . . . 38.4% |
| Talc | 2.0% |
| Salivary Inducing Agent | 2.0% |
| Water | |
| Ethanol | |

Example 6

Preparation of Calcium Carbonate Granules Containing Salivary Inducing Agent Coating The coating solution in Example 5 is applied to 500.0 g of calcium carbonate granules using a Glatt GPC-3 Wurster fluid bed coating unit at a spray rate of about 10-15 g/min, an atomization air pressure of about 2-2.5 bar, a product temperature of about 28-35° C., and an inlet temperature of about 45° C. until the granules were coated with a 10.0% Yes weight gain of the coating solution. The resulting coated granules contain, based upon the total dry weight of the coated granules, 0.2% of the salivary inducing agent.

The granules are then formed into tablets via compression to a hardness of approximately 6.3 kiloponds on a rotary tablet press equipped with ⅝ inch round flat-faced beveled edge tooling.

Example 7

Lozenge Containing Salivary Inducing Agent

A formulation for lozenges containing a salivary inducing agent is prepared using the materials described in Table 7.

TABLE 7

Lozenge Formulation

| Ingredients | Trade Name | Manufacturer | Mg/Unit |
|---|---|---|---|
| Corn Syrup NF | | | 400.0 |
| Sucrose NF | | Domino Sugar Inc. | 600.0 |
| Red Dye # 40 NF | | | 0.5 |
| Citric Acid Powder NF | | | 3.0 |
| Cherry Flavor | | International Flavors and Fragrances | 1.0 |
| Salivary Inducing Agent | | International Flavors and Fragrances | 1.0 |
| Total | | | 1005.5 |

For every 1000.0 g of mixture weighed from Table 7, 100.0 g of deionized water will need to be added to process the lozenges.

The corn syrup, sucrose and water are added to a pot, then heated to a temperature of about 140° C. with mixing. The dye and citric acid are added thereto with mixing, then the resulting solution is heated with stirring until it reaches 155° C. The mixture is then removed from the heat, and allowed to cool to 120° C., at which point the flavor and salivary inducing agent are added thereto with mixing.

The resulting mixture is then poured manually into preformed molds to form lozenges and are removed therefrom after reaching room temperature.

Example 8

Antacid Chewable Tablet Containing Salivary Inducing Agent

A blend for antacid chewable tablets containing a salivary inducing agent are prepared using the materials described in Table 8.

TABLE 8

Chewable Tablet Formulation

| Ingredients | Trade Name | Manufacturer | Mg/Tablet |
|---|---|---|---|
| Sucralose Powder NF | | Tate & Lyle | 10.0 |
| Dextrose Monohydrate NF | | | 556.3 |
| Calcium Carbonate USP | | | 400.0 |
| Crospovidone NF | Polyplasdone XL-10 ® | International Specialty Products | 16.7 |
| Magnesium Stearate NF | | | 8.0 |
| Peppermint Flavor | | International Flavors and Fragrances | 8.0 |
| Salivary Inducing Agent | | International Flavors and Fragrances | 1.0 |
| Total | | | 1000.0 |

The dextrose monohydrate and calcium carbonate are screened through a 20 mesh screen, then approximately half are added to a plastic bottle. The sucralose powder, peppermint flavor, crospovidone, and salivary inducing agent are then screened through a 50 mesh screen and added to the plastic bottle. One half of the remaining portion of dextrose monohydrate is then screened through the 50 mesh screen. All remaining dextrose monohydrate and calcium carbonate are then added to the plastic bottle. The components are blended end-over-end in the plastic bottle for 3 minutes. The magnesium stearate is then screened through a 50 mesh screen and added to the bottle, and blended end-over-end for an additional 1 minute.

The resulting blend is then compressed into tablets with a hardness of approximately 6.2 kiloponds on a rotary tablet press equipped with 5/8 inch round flat-faced beveled edge tooling.

We claim:

1. A method of administering a pharmaceutically active ingredient, said method comprising placing in the oral cavity a tablet comprising particles, wherein said particles comprise, based upon the total dry weight of the particle,:
   a) a core containing an active ingredient; and
   b) a taste-masking coating layer substantially covering the core, and
   c) from about 0.1% to about 25% of a salivation inducing agent layer substantially covering the taste-masking coating layer;
   wherein said particle has a size of from about 50 microns to about 1000 microns and wherein said method comprises chewing said tablet and/or allowing said tablet to disintegrate in the oral cavity prior to swallowing said tablet.

2. The method of claim 1, wherein the salivation inducing agent is selected from the group consisting of tasteless muscarinic acetylcholine receptor agonists; N, N-disubstituted phenylalkylamines wherein the alkyl has from about 1 to about 8 carbons; spirooxathiolane-quinuclidine; Heliopsis longpipes root; cholinesterase inhibitors; and mixtures thereof.

3. The method of claim 1, wherein the salivation inducing agent is selected from the group consisting of pilocarpine; N, N-disubstituted-2-phenylcyclopropylamines; spirooxathiolane-quinuclidine; Heliopsis longpipes root; cholinesterase inhibitors; and mixtures thereof.

4. The method of claim 1 wherein the salivation inducing agent has a salivation-inducing value of at least about 12%.

5. The method of claim 3 wherein the salivation inducing agent has a salivation-inducing value of at least about 12%.

6. The method of claim 1, wherein the active ingredient is a nonsteroidal anti-inflammatory drug, acetaminophen, pseudoephedrine, phenylpropanolamine, chlorpheniramine, dextromethorphan, diphenhydramine, dimenhydrinate, meclizine, famotidine, loperamide, ranitidine, cimetidine, astemizole, loratadine, desloratadine, fexofenadine, cetirizine, antacids, oxybutynin, methylphenidate, pharmaceutically acceptable salts thereof, and mixtures thereof.

7. The method of claim 5, wherein the active ingredient is a nonsteroidal anti-inflammatory drug, acetaminophen, pseudoephedrine, phenylpropanolamine, chlorpheniramine, dextromethorphan, diphenhydramine, dimenhydrinate, meclizine, famotidine, loperamide, ranitidine, cimetidine, astemizole, loratadine, desloratadine, fexofenadine, cetirizine, antacids, oxybutynin, methylphenidate, pharmaceutically acceptable salts thereof, and mixtures thereof.

8. The method of claim 1 wherein the tablet meets the USP dissolution specification for the 2000 Version of the USP for immediate release tablets containing the particular active ingredient.

9. The method of claim 7 wherein the tablet meets the USP dissolution specification for the 2000 Version of the USP for immediate release tablets containing the particular active ingredient.

10. A method of administering a pharmaceutically active ingredient, said method comprising placing in the oral cavity a tablet comprising particles, wherein said particles comprise, based upon the total dry weight of the particle,:

a) a core containing an active ingredient; and
b) a coating substantially covering the core, said coating comprised of from about 0.1% to about 25% of a salivation inducing agent;
wherein said particle has a size of from about 50 microns to about 1000 microns and wherein said method comprises chewing said tablet and/or allowing said tablet to disintegrate in the oral cavity prior to swallowing said tablet.

11. The method of claim 10, wherein the salivation inducing agent is selected from the group consisting of tasteless muscarinic acetylcholine receptor agonists; N, N-disubstituted phenylalkylamines wherein the alkyl has from about 1 to about 8 carbons; spirooxathiolane-quinuclidine; Heliopsis longpipes root; cholinesterase inhibitors; and mixtures thereof.

12. The method of claim 10, wherein the salivation inducing agent is selected from the group consisting of pilocarpine; N, N-disubstituted-2- phenylcyclopropylamines; spirooxathiolane-quinuclidine; Heliopsis longpipes root;

cholinesterase inhibitors; and mixtures thereof.

13. The method of claim 10 wherein the salivation inducing agent has a salivation-inducing value of at least about 12%.

14. The method of claim 12 wherein the salivation inducing agent has a salivation-inducing value of at least about 12%.

15. The method of claim 10, wherein the active ingredient is a nonsteroidal anti-inflammatory drug, acetaminophen, pseudoephedrine, phenylpropanolamine, chlorpheniramine, dextromethorphan, diphenhydramine, dimenhydrinate, meclizine, famotidine, loperamide, ranitidine, cimetidine, astemizole, loratadine, desloratadine, fexofenadine, cetirizine, antacids, oxybutynin, methylphenidate, pharmaceutically acceptable salts thereof, and mixtures thereof.

16. The method of claim 14, wherein the active ingredient is a nonsteroidal anti-inflammatory drug, acetaminophen, pseudoephedrine, phenylpropanolamine, chlorpheniramine, dextromethorphan, diphenhydramine, dimenhydrinate, meclizine, famotidine, loperamide, ranitidine, cimetidine, astemizole, loratadine, desloratadine, fexofenadine, cetirizine, antacids, oxybutynin, methylphenidate, pharmaceutically acceptable salts thereof, and mixtures thereof.

17. The method of claim 10 wherein the tablet meets the USP dissolution specification for the 2000 Version of the USP for immediate release tablets containing the particular active ingredient.

18. The method of claim 16 wherein the tablet meets the USP dissolution specification for the 2000 Version of the USP for immediate release tablets containing the particular active ingredient.

* * * * *